US005961214A

United States Patent [19]

Groth et al.

[11] Patent Number: 5,961,214

[45] Date of Patent: Oct. 5, 1999

[54] DETERMINING PROTECTIVE LAYER THICKNESS OF BLAST FURNACES

[75] Inventors: Richard J. Groth, Pittsburgh; Yongfu Zhao, Monroeville, both of Pa.

[73] Assignee: USX Corporation, Pittsburgh, Pa.

[21] Appl. No.: 09/220,898

[22] Filed: Dec. 24, 1998

Related U.S. Application Data

[62] Division of application No. 08/938,760, Sep. 26, 1997, Pat. No. 5,890,805.

[51] Int. Cl.[6] .............................. G01K 7/04; G01N 25/72

[52] U.S. Cl. ................................ 374/7; 374/166; 374/179

[58] Field of Search ............................... 374/4, 141, 137, 374/5, 6, 7, 166, 179

[56] References Cited

U.S. PATENT DOCUMENTS

| | | | |
|---|---|---|---|
| 2,264,968 | 12/1941 | DeForest | 374/7 |
| 2,987,685 | 6/1961 | Schaschl | 338/10 |
| 2,994,219 | 8/1961 | Schaschl . | |
| 3,018,663 | 1/1962 | Dunlop . | |
| 3,307,401 | 3/1967 | Bachman | 374/7 |
| 3,512,413 | 5/1970 | Von Krusentierna | 136/223 |
| 3,911,727 | 10/1975 | Katsuta et al. | 374/4 |
| 4,217,544 | 8/1980 | Schmidt | 324/65 CR |
| 4,248,809 | 2/1981 | Sakai et al. | 264/30 |
| 4,358,953 | 11/1982 | Horiuchi et al. | 374/7 |
| 4,412,090 | 10/1983 | Kawate et al. | 136/230 |
| 4,432,790 | 2/1984 | Bayewitz | 75/41 |
| 4,442,706 | 4/1984 | Kawate et al. | 73/86 |
| 4,479,727 | 10/1984 | Domingorena | 374/45 |
| 4,510,793 | 4/1985 | Ploegaert et al. | 73/86 |
| 4,513,384 | 4/1985 | Rosenvwaig | 374/4 |
| 4,539,846 | 9/1985 | Grossman | 73/547 |

FOREIGN PATENT DOCUMENTS 1290709 11/1989 Japan .

OTHER PUBLICATIONS

Evaluation of Mathematical Model for Estimating Refractory Wear and Solidified Layer in the Blast Furnace Hearth Suh Young–Keun, et al. ISIJ 1994 pp. 223–228.

*Primary Examiner*—Diego Gutierrez
*Assistant Examiner*—Maria Fernandez
*Attorney, Agent, or Firm*—W. F. Riesmeyer, III

[57] ABSTRACT

A method is provided for determining the thickness of a protective layer of solidified metal skull formed on the refractory hearth of a blast furnace. The refractory hearth has temperature probes embedded in the floor and walls thereof. The method includes periodically measuring temperatures indicated by the probes and determining the campaign maximum and current average temperature readings to locate two solidification isotherms representing the wear line of the refractory and the inner surface of the protective metal layer. The thickness of the protective layer is determined from the distance between the solidification isotherms representing the refractory wear line and the inner surface of the metal skull.

2 Claims, 5 Drawing Sheets

DETERMINING PROTECTIVE LAYER THICKNESS OF BLAST FURNACES

This is a Division of Application No. 08/938,760, filed on Sep. 26, 1997, now U.S. Pat. No. 5,890,805.

TECHNICAL FIELD

The present invention is of a method for extending the life of a blast furnace refractory lining and, and particularly to a method which includes on-line monitoring of campaign maximum and current average signals from a plurality of thermocouples embedded at spaced locations in the refractory lining and from a plurality of thermocouples embedded at spaced locations in a metal shell of the furnace, calculating from those signals the wear line of the refractory lining and the thickness of a layer of solidified metal skull formed on an inner surface of the refractory, and then determining the conditions of heat transfer at the shell e.g. whether or not a gap has formed between the refractory and the shell and whether or not water cooling of the shell is sufficient.

BACKGROUND ART

The iron blast furnace typically is constructed of a metal shell with a refractory brick lining. The life of the refractory brick lining determines the length of time that the furnace can be kept in operation before the furnace must be shut down for installation of new refractory. Longer refractory life decreases refractory cost and increases the productivity achieved from the furnace. More expensive refractory brick have been used to extend the length of a furnace "campaign". Grouting or gunning of refractory material between the refractory brick and the metal shell has also been used as a repair measure to close the gaps which sometimes form between the shell and the brick. Gaps between the brick and shell decrease heat transfer and cause increased wear of the refractory brick.

U.S. Pat. No. 4,510793 discloses the use of a ceramic bar in a furnace wall which wears with the lining. The wear of the bar and the lining is detected ultrasonically by generating ultrasonic pulses in the bar and detecting the reflection of the pulses from the worn inner end of the bar.

Japanese Published Application 1-290709 discloses thermocouples embedded in the refractory on the bottom and bottom side wall part of a blast furnace. From the temperatures measured by the thermocouples, calculations are made to determine the state of packing of coke in the core of the furnace. When the packing of coke is inadequate for preferential flow of molten iron in the central part of the furnace, changes are made in the amount, grain size or hot characteristics of the coke charged to the furnace.

U.S. Pat. No. 4,358,953, Horiuchi et al, discloses a method of monitoring the wear of refractory lining blast furnace walls by sensing temperatures at different points across the thickness of the refractory and analyzing the time delay between trigger signals representing internal phenomena of the furnace and the temperature probe output signals. This patent also describes a prior art method of determining the degree of wear from one dimensional heat transfer analysis. An apparatus for sensing temperature distribution in the refractory is also disclosed. A similar apparatus is disclosed in U.S. Pat. No. 4,412,090, Kawate et al, and in U.S. Pat. No. 4,442,706, Kawate, et al.

It is also known to use one-dimensional and two-dimensional heat transfer calculations to refractory temperature distributions and then later compare with measured temperatures to estimate remaining refractory and skull thickness. A method of this type is disclosed in a literature paper entitled "Evaluation of Mathematical Model for Estimating Refractory Wear and Solidified Layer in the Blast Furnace Hearth", by Suh Young-Keun et al, ISIJ, 1994, Pages 223–228. However, no method previously existed for using measured temperatures to calculate the thickness of the brick and skull directly in a manner which considers interaction between measured temperatures at all locations in a vertical plane simultaneously. Also, no previous method existed that could be used on-line without human intervention to signal problems with gap formation, inefficient cooling on the shell, and to discern the irregular "elephant-shaped" erosion profiles and "bowl-shaped" erosion profiles, so as to enable corrective measures to be taken during furnace operation in order to extend the life of the refractory.

Other patents related to the measurement of wall thickness and/or temperature include U.S. Pat. Nos. 2,264,968; 2,987,685; 2,994,219;3,018,663; 3,307,401; 3,512,413; 4,217,544; 4,248,809; and 4,539,846.

DISCLOSURE OF THE INVENTION

This invention is of a method for extending the life of refractory lining the interior of a metal shell of a blast furnace. The method includes placing thermocouples in the refractory at a plurality of spaced locations and monitoring the signals produced by the thermocouples during furnace operation. An average of the temperature readings at each thermocouple location is determined periodically and recorded. The maximum temperature reading since the beginning of a campaign of the furnace is also determined and recorded. From the current average and campaign maximum temperature readings from the thermocouple signals, a determination is made On-line, i.e. during furnace operation, as to whether a protective solidified layer of metal skull exists on the inner face of the refractory and the thickness of the skull. If no protective layer of solidified metal skull exists, or if it is of insufficient thickness, a determination is made as to whether a gap exists between the refractory and a metal shell of the furnace and the location of the gap or whether cooling of the metal shell is insufficient. Steps are then taken during furnace operation, based on the results of such calculations, to fill such gaps with refractory, to re-establish sufficient cooling of the shell or to form a protective solidified layer of sufficient thickness on the inner surface of the refractory. The method of this invention also includes performing a moving boundary calculation directly from measured temperatures at all thermocouple locations in a vertical plane simultaneously to discern irregular erosion profiles, e.g. "elephant-shaped" and "bowl-shaped" erosion of the refractory.

MODES FOR CARRYING OUT THE INVENTION

Figure 1:
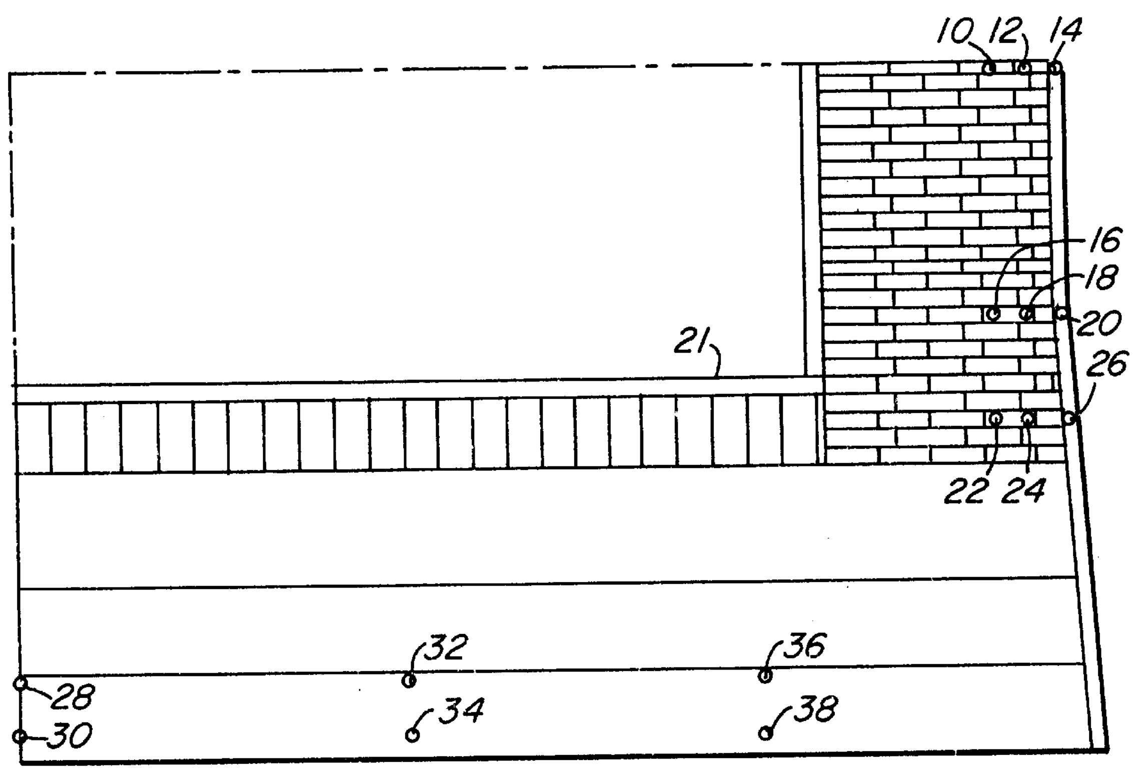
FIG. 1 is a cross-section of one-half of a blast furnace hearth showing the arrangement of thermocouples in the refractory and metal shell of the hearth area of the furnace.

Referring to FIG. 1, thermoprobes for measuring temperature, preferably thermocouples, are embedded in the refractory and the metal shell of a blast furnace in the hearth area. Thermocouples 10 and 12 are placed in the refractory sidewall of the hearth at two known positions across the thickness in a radial direction of the furnace. At least one thermocouple 14 is embedded at a known position in the metal shell in line with thermocouples 10 and 12 in the refractory. This first group of thermocouples is preferably placed at the elevation of a tap hole of the furnace and in the vicinity of the tap hole. A second group of thermocouples 16, 18 and 20 is placed at substantially vertically aligned positions with the first group at an elevation above the top surface 21 of the hearth pad. A third group of thermocouples 22, 24 and 26 is placed at substantially vertically aligned positions with respect to the first two groups at an elevation in the corner of the hearth sidewall where the sidewall meets the hearth pad. Thermocouple groups are placed in the floor of the hearth i.e. in the heart pad, at two known elevations with their hot junctions vertically aligned. One pair of thermocouples 28 and 30 is placed in the centerline of the furnace. A second pair of thermocouples 32 and 34 is placed one-third of the way to the inside of the metal shell at the hearth sidewall. A third pair, 36 and 38 is placed two-thirds of the distance to that location. It is preferred that thermocouples in this arrangement be placed spaced locations around the periphery of the furnace, with thermocouple coverage concentrated in the areas of the potentially highest wear such as around the tap hole.

Figure 2:
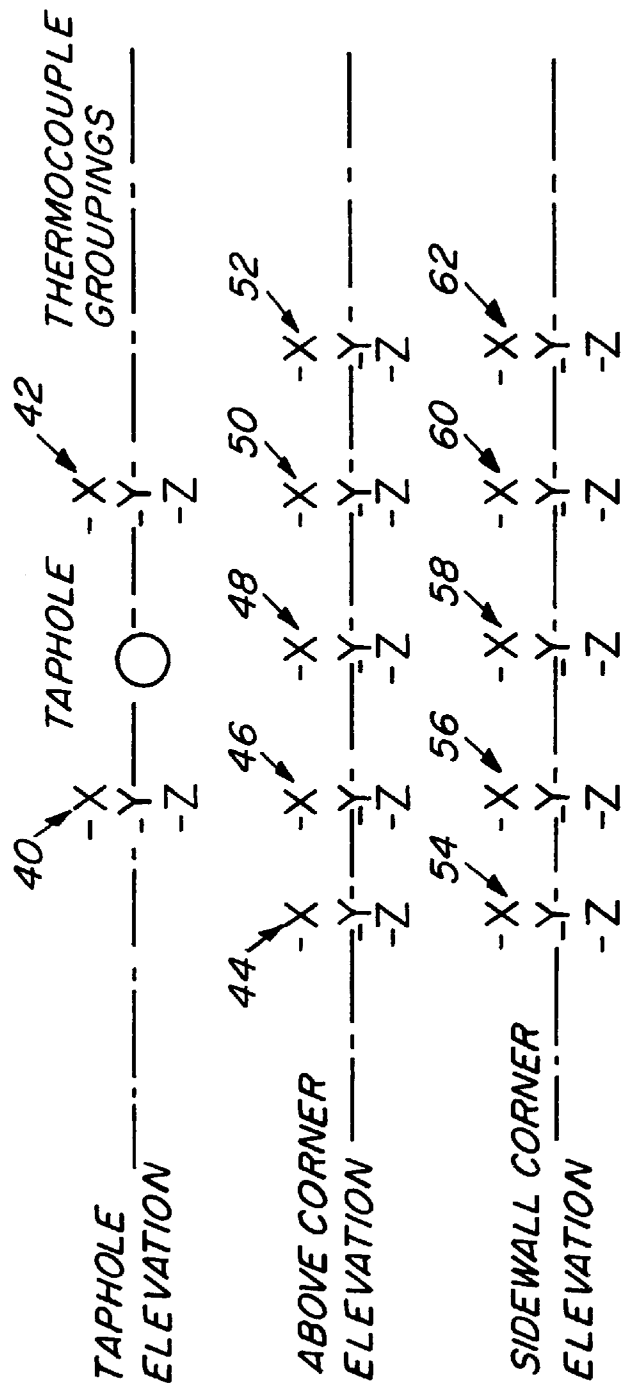
FIG. 2 is a schematic side elevation view of the tap hole area of a blast furnace illustrating the placement of thermocouples in that area.

Referring to FIG. 2, the placement of thermocouples around the tap hole area of the furnace is illustrated more specifically. Two groups of thermocouples 40 and 42 are located on either side of the tap hole at about the tap hole elevation. These thermocouples may be in-line in a horizontal direction normal to the plane of the drawing or spaced perhaps spaced about four inches (10 cm) from each other in the vertical direction as shown in FIG. 2. At an intermediate elevation above the top surface of the hearth pad, five groups of thermocouples 44, 46, 48, 50 and 52 are located in the tap hole area. Another five groups of thermocouples 54, 56, 58, 60 and 62 are located at about the elevation of the corner of the sidewall and the top surface of the hearth pad. The thermocouples in the latter two groups may be spaced about two feet (0.6096 meters) apart in a horizontal direction in the plane of FIG. 2.

Figure 3:
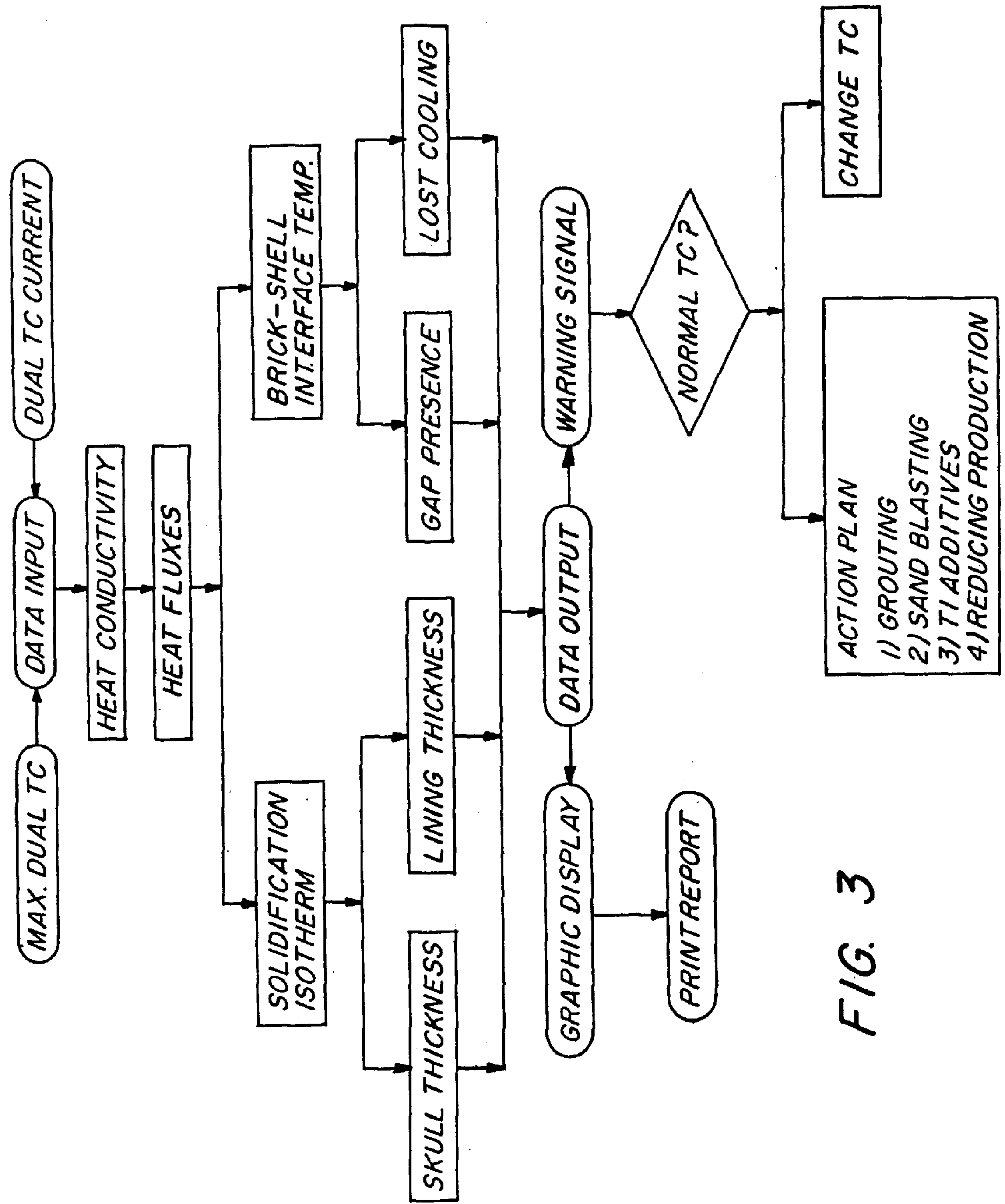
FIG. 3 is a flow diagram of steps taken in accordance with the method of this invention.
Figure 4:
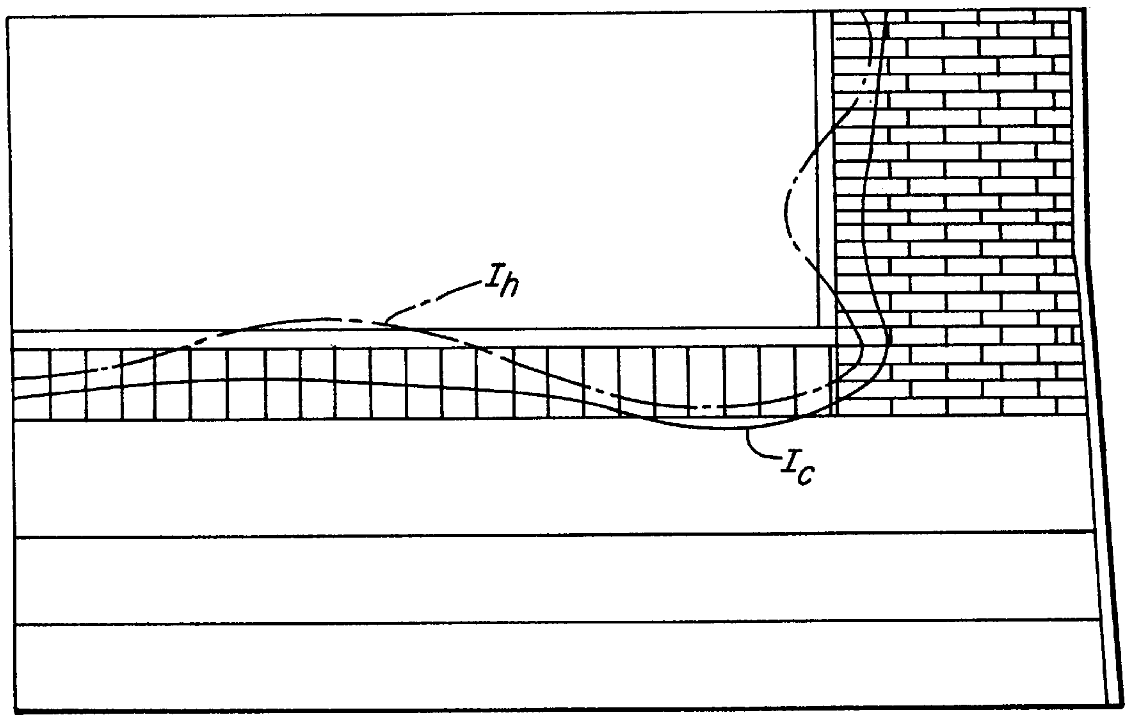
FIG. 4 is graphic representation of blast furnace hearth refractory lining wear and solidified metal skull formation determined according to the method of this invention.

As shown in FIG. 3, the readings taken from the plurality of thermocouples embedded in the refractory and shell are used as input in a computer program to carry out a sequence of heat transfer calculations. The current average and campaign maximum temperatures from these thermocouples are fed into a heat transfer model that translates these inputs into a heat flux. From this information, a one-dimensional heat transfer model calculates the location of the hot metal solidification isotherm, for example 2100° F. for blast furnace iron. The solidification isotherm which results from this calculation is used as the initial boundary in a two-dimensional heat transfer model. The two-dimensional heat transfer program iterates until a final boundary of the solidification isotherm is determined by minimizing the difference between the measured and predicted temperatures at each measuring point. The two-dimensional heat transfer calculations are made on the basis of the following two equations:

$$J = \int\int\left[\left(\frac{\partial T}{\partial x}\right)^2 + \left(\frac{\partial T}{\partial r}\right)^2\right] dx\,dr$$

$$\frac{\partial J}{\partial T} = 0$$

where T is the temperature at the location where the radius co-ordinate from the centerline of the furnace is r, and the height co-ordinate is x. By using the average and the maximum temperatures, the sequence of heat transfer calculation provides two solidification isotherm interfaces, Ih and Ic, respectively, as shown in FIG. 4. The interface Ih is closer to the hot side as compared with Ic. The isotherm interface Ic, which is closer to the cold side represents the wear profile of the refractory lining, while Ic represents the skull formation between hot metal and the lining. The distance between Ih and Ic represents the thickness of the solidified skull. The presence of the skull prevents the lining from the direct attack by hot metal and enables extending the life of the blast furnace hearth. The beginning of an irregular erosion profile in the corner are is illustrated in FIG. 4, where an “elephant-shaped” erosion is beginning to form as indicated by a greater erosion 62 in the corner than the erosion 64 in the adjacent sidewall. The method of this invention is able to determine “elephant-shaped” irregular erosion in an on-line calculation using a moving boundary calculation which considers interaction between measured temperatures at all locations in a vertical plane simultaneously.

The campaign maximum thermocouple readings represent the ultimate erosion profile of the refractory brick. Generally, the campaign maximum readings correspond to the highest heat flux and minimum calculated refractory thickness. These readings are then applicable to determine the critical isotherm corresponding to the actual erosion profile of the brick, Ic.

The average thermocouple readings represent the current condition within the hearth. The last hour's average temperatures recorded at each location is used to determine the current position of the critical isotherm and to calculate TIR and TIS, for purposes described hereinbelow, at all locations in the furnace hearth. The position of the current critical isotherm, Ih, relative to the isotherm corresponding to the maximum calculated refractory erosion profile, Ic, relates the presence and relative thickness of the protective skull on the inside surface of the refractory at each location. In general, when the current average thermocouple readings approach the campaign maximum temperatures, Ic~Ih, this indicates that there is presently no protective skull layer on the inside surface of the brick.

After calculating the critical isotherms, at each location, calculated values of TIR and TIS are used to determine the presence of a gap between the shell and the hearth brickwork and the presence of a build-up on the furnace shell.

$$TIR = T_2 - \left[\frac{(L_i - L_2)k_1(T)}{k_i(T)}\right]\left(\frac{T_1 - T_2}{L_2 - L_1}\right)$$

$$TIS = T_s + \left[\frac{(L_s - L_i)}{k_s(T)}\right]\left(\frac{T_1 - T_2}{L_2 - L_1}\right)$$

Where

TIR =Calculated shell interface temperature as calculated from hot side

Figure 5:
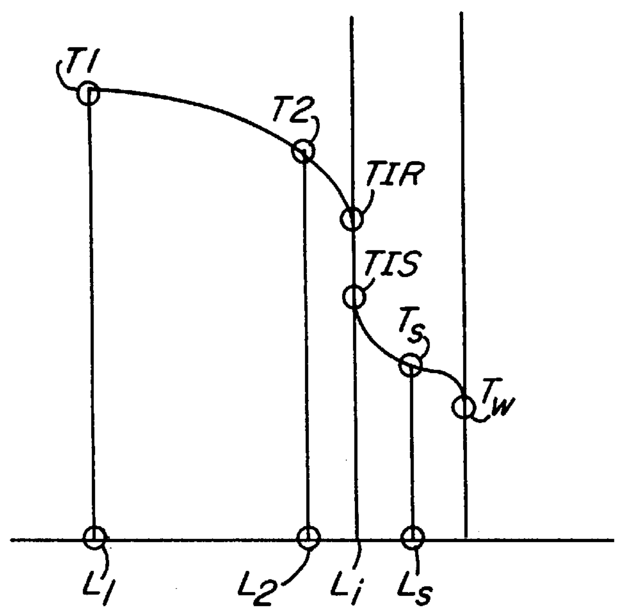
FIG. 5 is a schematic representation of two refractory-metal shell interface temperatures, TIR and TIS, determined by two different analyses, with TIR substantially greater than TIS, indicating the presence of a gap between the refractory and metal shell.
Figure 6:
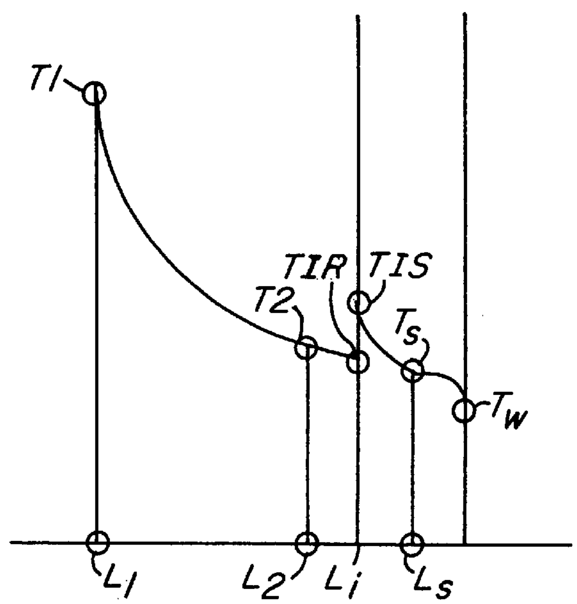
FIG. 6 is a schematic representation of the two refractory-metal shell interface temperatures, TIR and TIS, with TIS substantially greater than TIR, indicating insufficient cooling of the metal shell.

TIS =Calculated shell interface temperature as calculated from water cooled side $T_1$=Measured temperature from location 1, see FIGS. 5 and 6

$T_2$=Measured temperature from location 2, see FIGS 5 and 6

$T_s$=Measured shell temperature $L_i$=Relative position of shell interface as referenced from the coordinate system $L_1$=Relative position of thermocouple 1 as referenced from coordinate system $L_2$=Relative position of thermocouple 2 as referenced from the coordinate system $L_s$=Relative position of shell thermocouple as referenced from the coordinate system $k_1(T)$=Thermal conductivity as a function of temperature between locations 1 and 2

$k_i(T)$=Thermal conductivity between shell interface and location 2

$k_s(T)$=Thermal conductivity of the shell

Given these calculated values, the program then uses logical comparison statements to indicate potential warning conditions and directs appropriate action to alleviate any problems indicated.

As shown in FIG. 5, TIR and TIS are calculated and then compared to determine if a gap has formed. TIR is calculated according to the formula above from temperatures $T_1$ and $T_2$ at thermocouple locations 1 and 2 in FIG. 5 (which correspond, for example, to thermocouples 10 and 12 in FIG. 1). TIS is calculated using the formula above from temperatures Ts, $T_1$ and $T_2$ temperatures (where Ts corresponds to thermocouple 14 in FIG. 1). The following relation is used for that comparison:

If (TIR−TIS)>Preset limit (50° F. in one case), then a gap has formed between the refractory and the metal shell. The preset limit typically may be selected from within a range of from 20 to 120° F. Corrective action may be taken to fill the gap e.g. with a high conductivity grout material to re-establish contact with the cooled shell.

As shown in FIG. 6, TIR and TIS are calculated and then compared to determine if a build-up on the shell has occurred. The following relation is used for that comparison:

If (TIS−TIR)>Preset limit (50° F. in one case), then the water cooling on the shell is insufficient. Again the preset limit typically may be selected from within a range of from 20 to 120° F. Action may be taken to check for a problem in the water system or to determine if a potential build-up has formed on the outside surface of the shell which is interfering with proper heat transfer. After determining the cause of the problem, action may be taken to remove the build-up or to re-establish proper water flow in this area to improve heat removal efficiency. Conventional measures may be taken to correct these problems, for example, the shell surface may be sand blasted to remove any build-up or other measures may be taken to correct insufficient water flow or high temperature water.

Where there is no gap formed between the refractory and the shell and where cooling of the shell is sufficient and yet there is no solidified metal skull formed on the refractory lining of the furnace, or the thickness of the skull is insufficient to serve as protection for the refractory, measures may be taken to form a solidified metal skull of sufficient thickness to serve as protection for the refractory or to form additional refractory on the surface of the lining. Such measures may take the form of injecting or charging titanium-bearing materials into the furnace to protect the inner surface of the hearth, or reducing production and adjusting tuyere velocity to form a solidified metal skull of sufficient thickness.

Industrial Applicability

The invention is applicable to blast furnaces for producing iron for the steel industry as well as in blast furnaces for producing non-ferrous metals.

We claim:

1. A method of determining the thickness of a protective layer of solidified metal skull formed on the refractory hearth of a blast furnace wherein the refractory hearth has temperature probes embedded at spaced locations in radial directions from the center of the furnace and at various elevations across the thickness of the floor and walls thereof, comprising the steps of:

a. periodically measuring temperatures at said spaced locations in said radial directions and across the thickness of the furnace hearth floor and walls by the temperature probes embedded therein;

b. determining the maximum temperature recorded by each temperature probe since the beginning of a campaign of the furnace and the average temperature recorded by each temperature probe during a current time period;

c. analyzing the relation of said campaign maximum and current average temperatures of said temperature probes embedded in the hearth walls correlated with the radial distance between the temperature probes and the center of the furnace and the relation of said campaign maximum and current average temperatures of said temperature probes embedded in the hearth floor correlated with the elevation distance between the location of the temperature probes in the hearth floor so as to predict the location of the wear line of the refractory hearth from the location of a solidification isotherm closest to a metal shell, and to predict the location of the inner surface of a solidified metal skull lining said refractory hearth from an isotherm closest to the hot side of the furnace remote from the metal shell, and d. determining the thickness of the protective layer of solidified metal skull from the distance between the predicted wear line of the refractory hearth and the predicted inner surface of the metal skull.

2. A method according to claim 1 wherein said analysis is carried out by estimating the location of said solidification isotherms using a one dimensional heat transfer approximation, using this approximation as the initial boundary to begin a moving boundary calculation from a two dimensional heat transfer model, and continuing to iterate the two dimensional heat transfer model until a final boundary of each solidification isotherm is determined by minimizing the difference between the measured temperature at each temperature probe location and a predicted temperature at said location based on iterations of the two dimensional heat transfer model.

* * * * *